United States Patent [19]

Strowe

[11] 4,215,409
[45] Jul. 29, 1980

[54] FLOW CONTROL SYSTEM FOR ANESTHESIA APPARATUS

[75] Inventor: Robert J. Strowe, Summerville, S.C.

[73] Assignee: McKesson Company, North Charleston, S.C.

[21] Appl. No.: 886,132

[22] Filed: Mar. 13, 1978

[51] Int. Cl.$^2$ .................. G05D 11/00; A61M 17/00
[52] U.S. Cl. ......................... 364/510; 137/3; 222/25; 364/120; 128/203.14; 128/204.22; 128/205.23
[58] Field of Search ............... 364/500, 502, 510, 120, 364/564, 109; 128/184, 188; 73/194 R; 137/3; 222/23, 25, 26, 31, 3, 42; 340/606

[56] References Cited

U.S. PATENT DOCUMENTS

| | | | |
|---|---|---|---|
| 3,128,764 | 4/1964 | Koehn | 128/188 |
| 3,281,595 | 10/1966 | Rusz | 128/188 |
| 3,438,385 | 4/1969 | Nogami | 364/510 |
| 3,484,590 | 12/1969 | Stanton | 364/510 |
| 3,486,013 | 12/1969 | Stanton | 364/510 |
| 3,669,134 | 6/1972 | Dobritz | 128/188 |
| 3,831,447 | 8/1974 | Nogita et al. | 364/510 |
| 3,885,590 | 5/1975 | Ford et al. | 128/184 |
| 3,910,270 | 10/1975 | Stewart | 128/188 |
| 3,947,665 | 3/1976 | Hundley | 364/120 |
| 4,043,195 | 8/1977 | Hunting | 364/510 |
| 4,138,725 | 2/1979 | Ikemoto et al. | 364/510 |

Primary Examiner—Errol A. Krass
Attorney, Agent, or Firm—Paul & Paul

[57] ABSTRACT

An electronic analgesia/anesthesia apparatus is provided for the administration of a mixture of gases. This said apparatus has separate controls for independently increasing or decreasing the flow rate of each particular gas to be delivered thereby and includes an electrical circuit operatively connected to each control for driving a display indicative of the flow rate of the gas and a percentage calculator connected to each individual control for calculating the percentage of a particular gas with respect to the total gas flow and for displaying same; high and low pressure limit alarms and a pressure responsive safety control are included.

19 Claims, 6 Drawing Figures

FLOW CONTROL SYSTEM FOR ANESTHESIA APPARATUS

BACKGROUND OF THE INVENTION

Gas anesthesia has been used during medical and dental surgery for many years. Over a century ago, the discovery and use of ethyl ether as an anesthetic began. In fact, gas anesthesia has been used extensively because of the ready availability of ethyl ether. Later it was discovered that nitrous oxide ($N_2O$) had anesthetic properties and mixtures of oxygen and nitrous oxide are widely used today as anesthetics. Gas anesthesia provides certain advantages over drugs generally administered internally or intravenously in that it can be administered in continuous applications of minute quantities.

While all anesthetic substances, including the gaseous types, have some effect upon a patient, excessive amounts can be dangerous as they may adversely affect the functioning of vital organs. Therefore, it is important to be able to control precisely not only the amount of anesthetic administered to a patient but also the rate of gas flow and the percentage of a particular gas with respect to the total gas flow where more than one gas is employed.

As the administration of an anesthetic to a patient is so critical anesthetics are often administered along with oxygen, the oxygen being supportive to the functioning of a patient's vital organs. By changing the percentage of anesthetic and the percentage of oxygen it is possible to control the degree of anesthesia. Moreover, the anesthetic gas may be shut off and pure oxygen may be fed to the patient.

Gas anesthesia devices have been under development throughout this century. These devices, for the most part, have been directed toward the delivery of two or more gases through some type of mixing apparatus to a breathing mask positioned over the mouth and nose of a patient. Very early designs utilized pressure bottle supplies of oxygen and nitrous oxide or some other gaseous anesthetic. These two gases were often made available to the patient through a crude mixing valve structure via piping from each supply cylinder. A simple gate valve was also used at the supply cylinder for each gas.

Improvements to these designs concerned themselves with the metering of pressures of the gases in the administering apparatus and with the mixing of the two gases in certain proportions. As the previously available mixing valves were quite crude, another improvement in anesthesia apparatus was brought about by the introduction of the needle valve. Such needle valves provided a much more precise metering of the volume of gas passed through the valve as a function of the valve position. These needle valves permitted a calibration of the cross sectional area of the valve opening as a function of the number of revolutions the needle valve is rotated. Further improvements have incorporated check valves which permit the passage of gases in one direction only. These check valves prohibit the backing up of one gas into the other side of the system when the gas pressures are unequal.

The development of the single control, dual (or ganged) needle valve ushered in a more modern era of gas anesthesia apparatus. This valve comprises two needle valves, one for regulating oxygen flow and one for regulating anesthetic flow. These gauged, dual needle valves are mechanically linked together through a shaft and drive which rotate the needle valve shafts in opposite directions. The valves may be rotated to provide a proportional mix between oxygen and the anesthetic gas, wherein, at one extreme adjustment, the oxygen flow is fully open and the anesthetic gas flow cut off, and at the other extreme, the anesthetic gas flow is fully open and the oxygen flow is cut off. A control knob may be provided which is calibrated as a function of the percentage of each gas being administered to the patient. More precisely, the rotation of the control knob may be noted against a scale and correlated to read percentage of anesthetic being administered.

Koehn, U.S. Pat. No. 3,128,764 discloses an apparatus which supplies a mixture of nitrous oxide and oxygen to a patient. Koehn, as well as others, have used flow meters positioned in respective gas lines to provide a visual indication of rate of flow of the gas flowing therethrough.

The flow meters used by Koehn, as well as the flow meters incorporated into the apparatus discussed below, are of conventional design.

Flow meters usually comprise a vertically extending transparent tube having a ball therein of a specific gravity greater than the specific gravity of the gas being measured. The annular space between each ball and the inner surface of its respective tube and the velocity of the gas flowing upwardly through the tube determines the drag forces acting on the ball. When the stream of flowing gas produces a drag force on the ball equal and opposite to the force of gravity acting on the ball, the ball with reach a position of static equilibrium in the tube. As the flow rate varies, the position of the ball in the tube varies accordingly so that the particular position of the ball in the tube indicates a particular flow rate. A calibrated scale is disposed adjacent the tube and indicates the rate of flow of the respective gas as measured by the ball within the tube.

While these improvements have advanced the state of the anesthesia art, the development has not yet reached the point where these devices are sufficiently presice and simple and reliable. Even with these improvements in anesthesia apparatus, mistakes continue. These mistakes, while sometimes due to failures in the equipment, are often due to mistakes on the part of the operator to properly adjust or monitor the operation of the equipment, perhaps while acting under adverse conditions, or perhaps while under stress or a state of exhaustion and most certainly while his attention is at least partially diverted to additional activities which must be performed simultaneously with the operation of the anesthesia equipment. Analog equipment of the type discussed above, has not proven entirely satisfactory.

The need persists for reliable, easy to operate, and easy to adjust anesthesia apparatus. Presently the operator must deal with an analog reading of his adjustment knob. His interpretation of the setting is a function of how finely he can read the analog scale, as well as, from what angle he is viewing the scale. It is well known that the interpretation of an analog scale will vary with the angle from which it is read.

An object of this invention is to provide a flow control system for an anesthesia apparatus having a direct, mechanically operated, on-line gas flow rate adjustment and a visual display of the instantaneous adjustment, wherein this display provides a digital read out of flow rate.

A second objective of this invention is to provide such apparatus wherein said display is driven by a calculation component responsive to the flow rate adjustment.

Another objective of this invention is to provide such an apparatus having at least two such on-line gas flow rate adjustments for individually and independently adjusting the flow rate of each gas wherein a display of percentage gas mixture is presented in an alphanumeric digital display.

Another object of this invention is to provide such an apparatus having separate visual displays for each flow rate adjustment, including selectively a digital readout of flow rate, wherein each display is individually driven by a separate calculation component responsive to a separate flow rate adjustment.

A further object of this invention is to include calculation circuitry responsive to all of the separate flow rate adjustments for driving a separate visual display as representative of the percentage of a single gas flow to the total gas flow.

An even further object of this invention is to provide a digital encoder as part of each separate flow rate calculation component and a percentage calculation circuit as part of the percentage gas flow circuitry.

A further object of this invention is to provide a pressure sensor interlock which permits flow of the anesthesia gas only in the presence of the flow of oxygen.

Another object of this invention is to provide pressure limit alarm sensors on both supply inputs to the flow control apparatus, these sensors alarming when the supply gas pressures are greater than or less predetermined pressure limits.

SUMMARY OF THE INVENTION

The objects of this invention are realized in an electronic analgesia/anesthesia machine for administering anesthetic gases and oxygen to a patient. Such a machine may have a straight-through configuration wherein the flow rate of each of the individual gases may be completely independently increased or decreased by means of a control valve situated therein, without affecting the flow rate of another gas. Such a machine may mix the gases only at the output manifold.

Included may be both upper and lower pressure sensing alarm switches in each of the supply lines of each gas supplied to the machine. Preferably oxygen is used as the basic life support gas processed through the apparatus.

Separate control knobs are directly coupled to each valve for controlling the flow rate of each gas. These control knobs are each mechanically coupled to separate electrical switches having detents for operation which positively defines a fixed number of positions thereof. Separate electronic calculating circuits may be connected to each switch to independently compute the flow rate through each valve. Additional electronic circuitry may be connected to additional similar switch structure to calculate the percentage volume of a particular gas with respect to the total gas passing through all valves. Digital displays may be connected to each circuit for alphanumerically displaying each output.

DESCRIPTION OF THE DRAWINGS

The advantages, features and operation of the invention can easily be understood from a reading of the following detailed description of the invention in conjunction with the attached drawings and wherein like numerals refer to like elements and in which.

DETAILED DESCRIPTION

An electronic analgesic/anesthetic apparatus has a straight-through gas flow configuration. Two individual gases, such as oxygen and nitrous oxide, are handled by the machine, completely independently of one another. At the output of the apparatus, an output manifold or joining tube permits the mixture of the two gases handled therethrough. The increasing or decreasing of the flow rate of one gas will not affect the existing flow rate of the other. Gas flow rates are displayed either as a digital readout or by conventional analog flow tubes. The user has the option of either, but not both, flow rate displays.

In addition to flow rate, the apparatus electronically calculates the percentge of nitrous oxide ($N_2O$) in the output gas. This percentage is displayed on a digital readout which may be located on a front panel of the apparatus. This digital display is presented at all times when the unit is operating. The unit does not perform chemical analysis of the output gas but calculates output gas percentage by volume on the basis, of individual flow rates.

Numerous safety devices are incorporated into the apparatus. A gas interlock stops the flow of nitrous oxide when there is a loss in oxygen pressure. A high-low pressure alarm system monitors the input line pressures for excessively high or excessively low supply pressures. A direct oxygen flow valve facilitates a high oxygen flow of approximately 45 liters per minute which may be used in emergency situations or for flushing the unit or the equipment to which the unit is connected.

Figure 1:
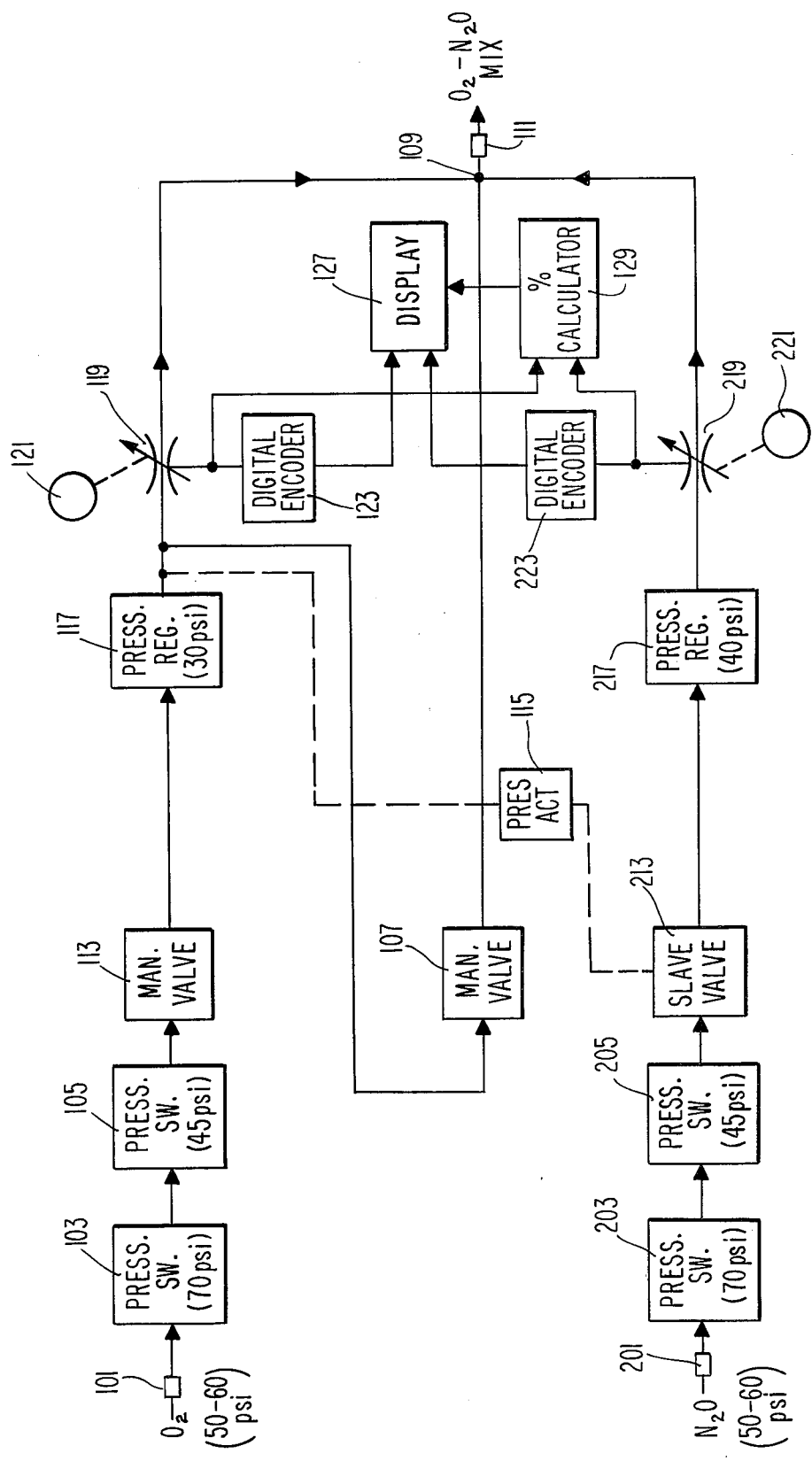
FIG. 1 shows a flow diagram of an anesthesia machine for administering nitrous oxide anesthetic and oxygen wherein the interrelationship of the structural elements is illustrated.

Referring now to FIG. 1, oxygen is supplied normally at between 50 and 60 PSI and enters the apparatus through an appropriate D.I.S.S. fitting 101 which leads to the oxygen side of the apparatus. Similarly, nitrous oxide being supplied at approximately 50 to 60 PSI enters the nitrous oxide side of the apparatus through an appropriate D.I.S.S. fitting 201. Each gas line, i.e., the oxygen side and the nitrous oxide side, is monitored by a pair of high and low pressure sensitive actuators 103, 203, 105, and 205, respectively. Connected to the oxygen fitting 101 is the oxygen high pressure switch 103 which operates when the line pressure exceeds a fixed pressure such as 70 PSI. Connected in line and downstream from the oxygen high pressure switch 103 is an oxygen low pressure switch 105 which operates when the line pressure drops below a fixed pressure, as an example 45 PSI. Likewise, connected directly to the nitrous oxide fitting 201 is a nitrous oxide high pressure switch 203 which operates when the line pressure exceeds 70 PSI and downstream from the high pressure switch 203 is a low pressure switch 205 which operates when the nitrous oxide line pressure drops below 45 PSI. Each of these actuators 103, 203, 105, and 205 is connected directly to a gas warning system. Should the supply pressure go beyond the limit established by the actuators, an audible alarm will sound and a visual indicator describing the malfunction will be energized. As such, each of the individual pressure switches 103, 203, 105 and 205 may be connected directly to a distinct visual indicator bulb which may be located at any conspicuous place on the apparatus to light the particular bulb which is indicative of the particular malfunction.

Connected directly to the oxygen supply on the downstream at the oxygen side of pressure regulator 117 described below is a manual flush valve 107. The down pressure side of the flush valve 107 is connected directly to an output manifold mixing point 109. While this mixing point 109 is represented as a point on the flow diagram, FIG. 1, it is in reality an output pipe wherein gas lines connected thereto meet and mix the gases as they are then connected to an output fitting 111. While the flow rate of oxygen shunted directly to the output point 109 through the flush valve 107 was given as 45 liters per minute, this value in fact, is a nominal value.

Downstream from the low pressure switch 105 in the oxygen tubing side of the apparatus is a mechanical "on"-"off" valve 113. This valve 113 is operated directly from an "on" "off" safety key on the device and turning off this "on-off" valve 113 will stop all gas flow passing through the mixing portions of the apparatus. Down line from the oxygen "on-off" valve 113 is the pressure regulator 117. A pressure actuator 115 is connected to the downstream side of the pressure regulator 117. This actuator 115 senses whether there is any pressure in the oxygen tubing supplied by the pressure regulator 117 and if this pressure is within tolerance, the output of this actuator 115 is mechanically coupled to operate a slave valve 213 in the nitrous oxide side of the apparatus.

The nitrous oxide slave valve 213 is connected to the downstream side of the low pressure switch 205. Oxygen "on-off" valve 113, pressure actuator 115, pressure regulator 117 and nitrous oxide slave valve 213 operate to shut the operation of the apparatus down when the safety key is turned off. The nitrous oxide supply through the apparatus will also be shut down when the oxygen supply has been lost. The pressure actuator 115 operates to open the nitrous oxide slave valve 213 when the pressure sensed exceeds a nominal threshold such as 30 psi.

As an alternative to the embodiment discussed above, the nitrous oxide slave valve 213 may be pneumatically operated, wherein the actuator 115 provides a pneumatic control signal to activate the nitrous oxide slave valve 213. With the absence of oxygen pressure, the activating pneumatic control pressure is absent and the valve 213 is biased to automatically shut off.

Oxygen pressure regulator 117 is adjusted to supply oxygen at a regulated pressure such as approximately 30 PSI. Connected to the downstream side of the slave valve 213 is a nitrous oxide pressure regulator 217. This pressure regulator 217 is adjusted to supply nitrous oxide at a regulated pressure of about 40 PSI.

A tapered oxygen needle valve 119 being directly and mechanically coupled to a control knob 121 is connected between the output of pressure regulator 117 and the mixing point 109. The position of the needle valve 119 will determine the volumetric flow of oxygen to the output mixing point 109. The needle valve 119 is of a standard configuration having a conically tapered valve surface for seating against a mating surface of a housing portion thereof. A shaft extension of the conical seating surface includes a screw thread portion, wherein, as control knob 121 is rotated, the needle valve is screwably closed or opened to pass varying amounts of oxygen. The volumetric flow of oxygen therefore will be a function of the supply pressure at the valve 119 (30 PSI) and the cross sectional area through the valve 119.

Connected to the output side of nitrous oxide pressure regulator 217 is a second needle valve 219 which is operated, mechanically linked to, and controlled by a control knob 221. The configuration of the nitrous oxide needle valve 219 and its control knob 221 is identical to that of the oxygen valve 119 and its control knob 121. The volumetric flow of nitrous oxide will be a function of the nitrous supply pressure (40 PSI) and the instantaneous cross-sectional opening of the nitrous oxide needle valve 219.

Mechanically coupled to the first needle valve 119 is a first digital encoder 123; mechanically coupled to the second or nitrous oxide needle valve 219 is a second digital encoder 223. Digital encoders 123 and 223 are electrically coupled to a digital display 127. Similarly mechanically coupled to the first and second needle valves 119 and 219 is a percent calculator 129. The percentage calculator 129 is electrically coupled to the digital display 127.

The individual digital encoders 123 and 223 electronically translate the mechanical position of their respective, coupled, needle valves 119 and 219 are computate the rate of flow therethrough based upon the regulated pressure supply thereto. These rates of flow are each individually and continuously displayed on digital display 127 in alphanumeric presentation.

Percentage calculator 129, being mechanically linked to both the valves 119 and 219, electronically translates their positions to perform a percentage calculation of the total gas supplied to the mixing point 109. This percentage calculation is separately and continuously displayed on the digital display 127 in the form of an alphanumeric percent nitrous oxide. A mechanical to electrical connection between the valves 119 and 219 and the electronic digital encoders 123 and 223 and percentage calculator 129 is shown in part in FIG. 2.

Figure 2:
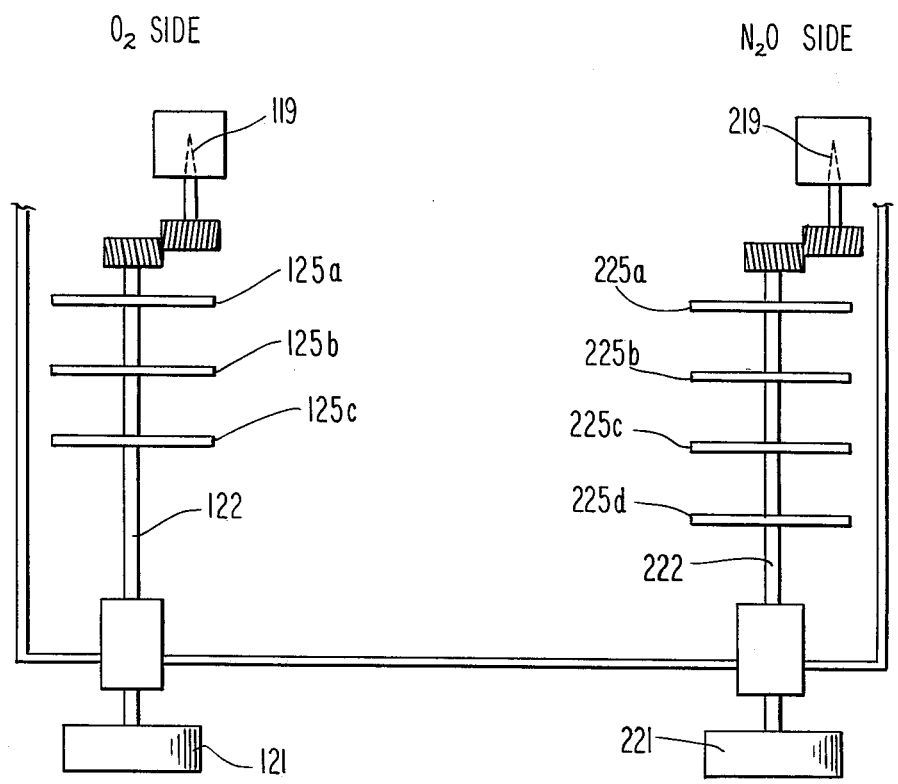
FIG. 2 shows the needle valve and control knob interconnection and electrical wafer switches for the anesthesia machine in FIG. 1.

FIG. 2 shows a mechanical configuration of the oxygen needle valve 119 and the nitrous oxide needle valve 219 with their respective control knobs 121 and 221 coupling. Control knob 124 is directly coupled to the needle valve 119 via a control shaft 122. Positioned on the control shaft 122 are three identical wafer switches 125a, 125b, and 125c. These wafer switches 125a, 125b, and 125c are of a standard type commonly used in the electrical arts and include a wiper and detented positions which index positive positions of rotation. Similarly for the nitrous oxide side of the apparatus, control knob 221 is directly coupled to the needle valve 219 via a control shaft 222. Control shaft 222 being directly mechanically coupled to valve 219 and containing four identical wafer switches 225a, 225b, 225c, and 225d similar to wafer switches 125.

Figure 3:
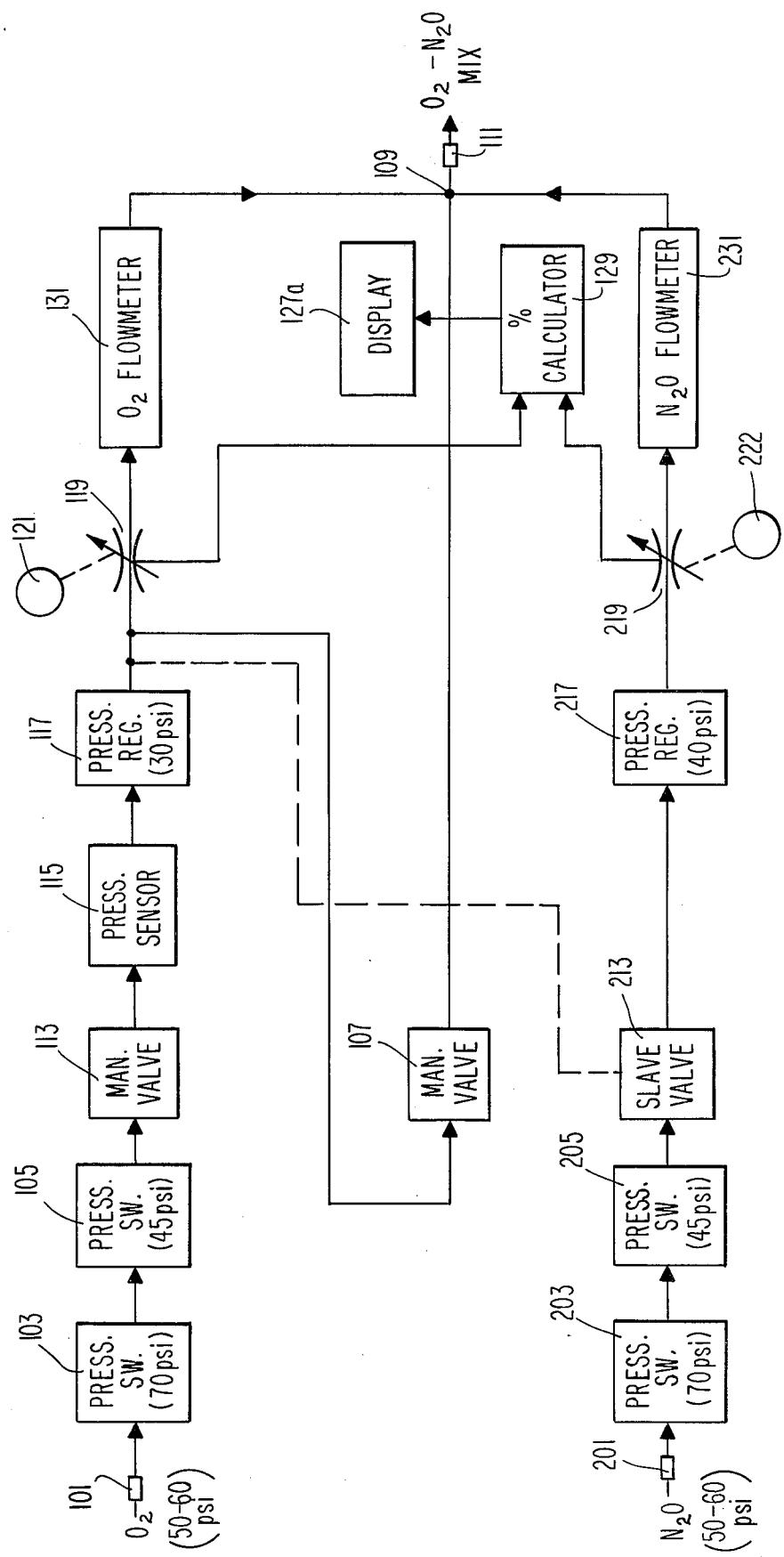
FIG. 3 shows an alternate embodiment of the invention of FIG. 1 in flow diagram format, wherein flow meters are introduced into the flow paths of the oxygen and nitrous oxide while the digital encoders are disconnected.

As an alternative to the configuration of FIG. 1, flow meters of a conventional configuration may be inserted into each of the oxygen and nitrous oxide gas lines, FIG. 3. This alternate embodiment, FIG. 3, has an identical configuration up to the point of the needle valves 119 and 219 as the apparatus shown in FIG. 1. However, in this alternate configuration, FIG. 3, the valves 119 and 219 are electrically connected only to a percentage calculator 129. The percentage calculator drives an alphanumeric digital display 127a. The display 127a differs from the original display 127 in that there is an absence of display of individual flow rates of the individual oxygen and nitrous oxide gases. Flow rates of the individual oxygen and nitrous oxide gases are displayed via oxygen flow meter 131 and nitrous oxide flow meter 231, respectively. The oxygen flow meter 131 has its input connected to the output of the needle valve 119 and its output connected to the mixing point 109. Likewise, the nitrous oxide flow meter 231 has its input connected to the output of the needle valve 219 and its output connected to the mixing point 109.

Digital encoders 123 and 223 are in fact electronic flow rate calculators. With knowledge of the proper choice of gas supply pressure and orifice size as correlated to rotational position of valve shaft 122, and 222, oxygen and nitrous oxide flow rate each individually computated. The wafer switches 125z, 125b, 125c, and 225a, 225b, 225c, and 225d, as shown in FIG. 2, are for a particular application 32-position single wiper detended electrical decks.

Figure 4:
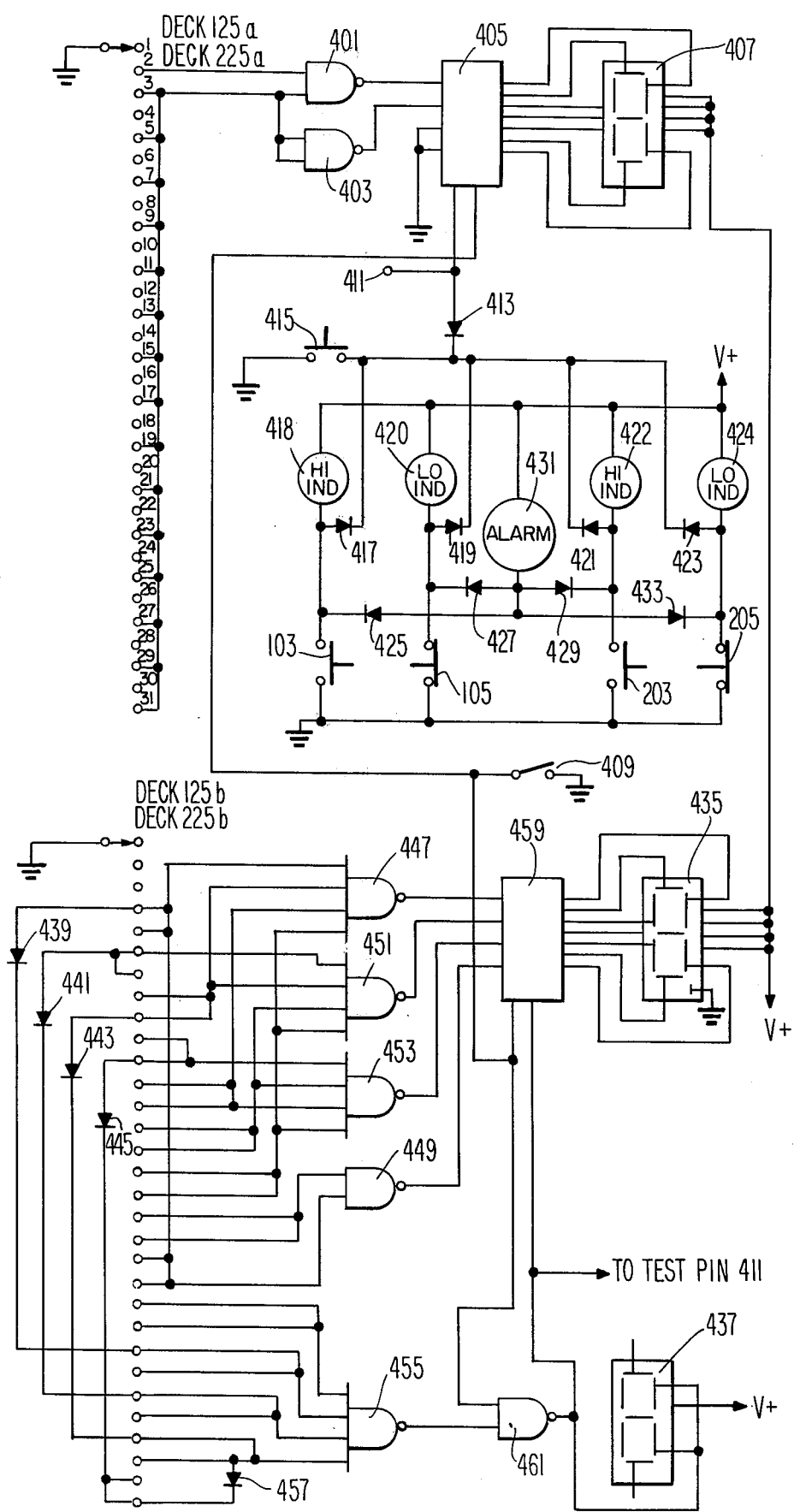
FIG. 4 is a circuit diagram of the circuitry of the digital encoder of FIG. 1 and its associated digital display, which circuitry as illustrated, presents certain identical electrical structure for both the oxygen and nitrous oxide flow paths in singular.

FIG. 4 shows the digital encoders 123 and 223 flow rate calculation circuitry, the electronics for which is identical for both the oxygen and the nitrous oxide side of the apparatus and therefore presented in singular. Deck 125a is used to encode 0.1's and 0.5's liter increments while deck 125b is used to encode whole liters in "units" and "tens" quantities. The wiper of the deck 125a, or 225a is tied to ground. The first postition as well as every even numbered position 4 on, is left open. The second position on the deck 125a is tied to one input of a first NAND gate 401. Position 3 and 5 and every other odd numbered position on the deck 125a is tied together and to a second input of the first two input NAND gate 401. A second two input NAND gate 403 has both of its inputs tied together and connected to the second input of the first NAND gate 401, which is in turn ganged connected to the sequence of odd numbered positions of the deck 125a. The first and second NAND gates 401 and 403 are a type "SN4700" NAND gate. The output of the first NAND gate 401 is connected to the "A" input of a "SN7447" type decoder driver 405. The output of the second NAND gate 403 is connected to the "C" input terminal of the driver 405, while the "D" and "B" inputs are connected to ground. The outputs of the driver 405 are connected to a seven-segment display 407. The outputs of the decoder driver 405 are connected to the seven-segment display 407 in a conventional manner. Also connected to the seven segment display 407 is the supply voltage. As the wiper of the deck 125a is stepped down through the various positions and the display 407 displays increments of gas flow.

FIG. 4 also shows representative electrical circuitry for activating a "units" and "tens" seven element light emitting diode digital display. The "units" display 435 is activated by the operation of a second deck 125b for the oxygen (and the nitrous oxide) circuits respectively. As the electrical circuitry for both the oxygen and nitrous oxide circuits is identical, FIG. 4, shows this circuitry in singular.

The blanking input of the decoder driver 405 is connected to a flow tube switch 409. With switch 409 closed, the blanking pin of decoder driver 405 is connected directly to ground. This will turn the display 407 off and effectively cut the encoder 123 out of the system. The test input of the decoder driver 405 is connected to a test circuit through isolation diode 413. Activation of the test switch 415 enables all outputs of the decoder driver 405 exhibiting on "8" readout of the display 407. This test is conducted to test the proper operation of the display 407.

The deck 125b is identical to the deck 125a, being a 32-position wafer switch with a single wiper and having detents for positive recognition of rotational position. The positions, 1, 2, 3, and 32 of the deck 125b are left open and the wiper is tied to ground. Position 4 is connected to position 24 through a tenth diode 439 with the anode of this diode 439 being tied to position 4. The positions 6 and 7 are connected together and in turn, connected to the anode of an eleventh diode 441 which is connected on its cathode to position 26. Position 9 is connected through a twelfth diode 433 to position 28 with the diode 443 being connected on its anode to position 9. The position 11 is connected to positions 30 and 31 through a thirteenth diode 435 with the diode 435 being connected on its diode side to position 11 and on its cathode side to positions 30 and 31. Switch position 4 and 5, 20 and 21 are connected together and also connected to a first input of a third type "SN7400" to input NAND gate 449. Position 6 is connected to a first input of a second type "SN7420" four input NAND gate 451. Positions 8 and 9 are each connected in common to the second input of the NAND gates 447 and 451. Positions 10 and 11 are connected in common to the first input of a third type "SN7420" four input NAND gate 453. Positions 11 and 13 are each connected in common to the third inputs of the HAND gates 447 and 453. Positions 14 and 15 are each connected in common to the third input of NAND gate 451 and the second input of NAND gate 453. Positions 16 and 17 are each connected in common to the fourth input of NAND gates 447, 451, and 453. Positions 18 and 19 are connected in common to the second input of the NAND gate 449.

Positions 22 and 23 are connected in common to a first input of a fourth type "SN7420" four input NAND gate 455. Positions 24 and 25 are connected in common to the second input of this NAND gate 455. Positions 26 and 27 are connected to the third input of this NAND gate 455. Positions 28 and 29 are connected to the fourth input of this NAND gate 455. The fourth input of the NAND gate 455 is also connected through a fourteenth diode 457 to position 31. The diode 457 being connected to anode to NAND gate 455 and cathode to switch position 31. The output of first four input NAND gate 447 is connected to a first input of a second BCD-to-seven segment decoder/driver 459. The output of the second four input NAND gate 451 is connected to a second input of the second BCD-to-seven segment decoder/driver 459, while the output of the NAND gate 453 is connected to a third input of the decoder/driver 459 and the output of the third two input NAND gate 449 is connected to a fourth input of the decoder/driver 459. The ripple blanking pin of the first decoder/driver 405 is connected to the blanking pin of the second decoder/driver 459. The lamp test pin of this second decoder/driver 459 is connected to test pin 411.

The outputs of the BCD-to-seven segment decoder/driver 459 are connected in standard configuration to the second seven segment display 435. The display 435, also, has voltage connections for supplying power thereto.

The blanking pin of the first and second decoder/drivers 405 and 459 are connected to a first input of a fourth type "SN7400" two input NAND gate 461. The output of the fourth four input NAND gate 455 is connected to the other input of this fourth two input NAND gate 461. The output of this latter two input NAND gate is connected to power an alphanumeric "1" of the third seven segment display 437 for the 0.1's liter per minute display and is connected to the lamp test pin of the second decoder/driver 459.

With the electrical configuration as shown in FIG. 4, the seven-segment displays 407, 435 and 437 can provide an alphanumeric display of gas flow in liters per minute from 00.0 to 19.9. These display elements 407, 435 and 437 from part of the digital display 127 of FIG. 1.

The alarm circuit is controlled by two groups of two pairs of pressure acutated switches 103, 105, and 203, 205 with one group monitoring each gas line, oxygen and nitrous oxide respectively. Actuator switch 103 provides an electrical closure should the oxygen pressure exceed a limit, while the other pressure actuator switch 105 provides a closure when the oxygen pressure falls below a set limit. The switchs 103, 105 are connected directly to appropriate indicators 418, 420, respectively, located at the display 407. These switches are also connected to an audible alarm 431 through a diode isolation network 425, 427, 429, 433.

Similarly actuator switch 203 provides an electrical closure should the nitrous oxide exceed a limit while a corresponding second pressure actuator switch 205 provides a closure when the nitrous oxide pressure falls below a set limit. The switches 203, 205 are connected directly to appropriate indicators 422, 424, respectively, located at the display 407. These switches are also connected to an audible alarm 431 through the diode isolation network 425, 427, 429, 433.

The alarm circuit works so that when the test switch 415 is activated, the high indicator lights 418 and 422 and low indicator lights 420 and 424 and the audible alarm 431 are all activated. The respective high and low pressure switches 103, 203, 105, 205 operate to activate the respective individual lights 418, 422, 420, and 424, respectively, and in parallel, activate the audio alarm 431.

Figure 5:
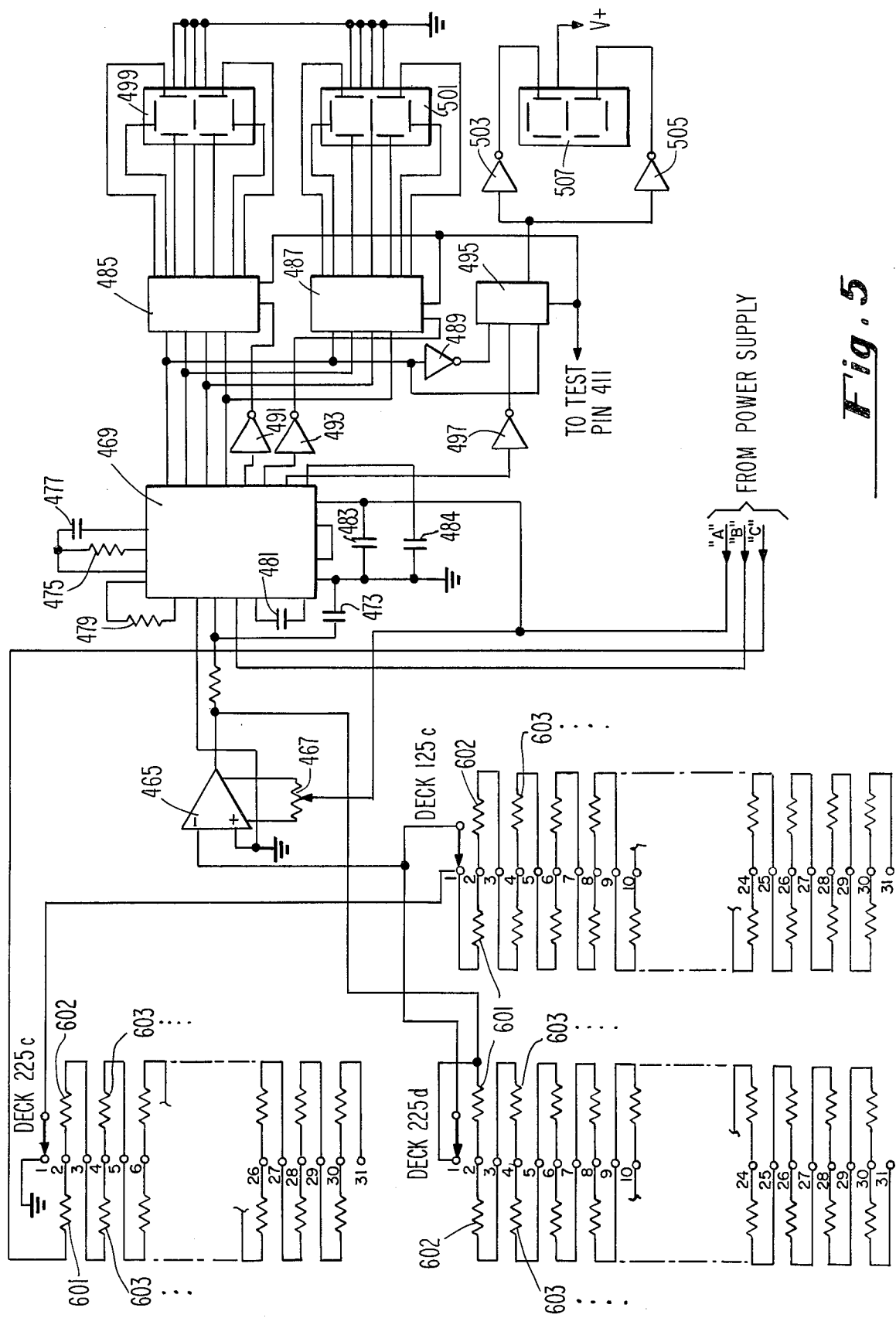
FIG. 5 is a circuit diagram of the electrical circuitry for performing the percentage calculation as well as its associated digital display.

The percentage calculation circuitry 129 of FIG. 1 is shown in more detail in FIG. 5. This circuitry utilized deck 125c on the oxygen control shaft and decks 225c and 225d on the nitrous oxide control shaft. Each of the decks 125c, 225c, and 225d has 30 resistors 601, 602, and 603 connected thereto in identical configuration. These resistors are connected between each of the positions numbered 2 through 31 on each of the decks with resistor 601 being connected to position 2; resistor 602 connected between positions 2 and 3; and a plurality of resistors 603 connected one each between the remaining positions. The decks 125c, 225c, and 225d each provide a segmented resistance network wherein first a 1K Ohm resistance 601 then an additional 4K Ohm resistance 602 then additional 5K Ohm resistances 603 are successively added from the toal electrical resistance as the wiper is successively moved from position to position.

The deck 225c has its number 1 position connected to ground and the wiper connected to the number 1 position of deck 125c. The wiper of the deck 125c is connected in common with the wiper of the deck 225d and with the inverting input of a first operational amplifier 465. Amplifier 465 is typically a Motorolla-type "MC 1458". The second position on deck 225c is connected through the resistor 601 to the "C" voltage connection from the power supply described below. Deck 225d also has its number 1 position connected to its 2nd position through the resistor 601. Likewise with deck 125c the number one position is connected to its 2nd position via the resistor 601. The non-inverting input of the operational amplifier 465 is connected to ground. The balancing circuit of the amplifier 465 contains a resistance 467 having a maximum resistance of 10K Ohms and a wiper thereto. The output of the operational amplifier 465 is connected to the input of a Motoralla-type "14333B' analog-to-digital (A/D) converter 469 via an 8.2K Ohms resistance 471. Position 1 of the deck 225d is connected directly to the output of part of the operational amplifier 465. Thus the resistor network of deck 225d forms the feedback circuit of amplifier 465 (Classical R2). The composite input resistance (Classical R1) is composed of the series resistance of decks 125c and 225c. It can be noted that a proper choice of reference voltage can scale the output voltage from the amplifier 465 as a direct function of the percentage, i.e., assume 1 volt is 100% nitrous oxide. The voltage output from amplifier 465 is therefore scaled to 1 volt scale. This voltage can be simply converted to a digital format.

The A/D converter may have associated noise and timing components connected as per manufactures recommendations. These components used herewith include:

| Capacitor 473 | .1 mf |
|---|---|
| 477 | .1 mf |
| 481 | .1 mf |
| 483 | .1 mf |
| 484 | .1 mf |
| Resistors 475 | 180 K |
| 479 | 300 K |

The BCD coded outputs from A/D converter 469 are connected to the inputs of a 1st and 2nd latch/decoder/ driver 485, 487, respectively in normal configuration. These latch/decoder/drivers 485, 487 each being of a type Motorolla "MC14511."

A Motorolla-type "MC14027", J-K type flip flop 495 is used as a storage element for the most significant output of the A/D converter 469. Specifically, flip flop 495 has its J input tied to the output of the first inverter 489. The clock input to this J-K flip flop 495 is connected to the seventh output of the A/D converter 469 via a fourth inverter 497. The K input to the J-K flip flop 495 is connected in common with the inputs of the third and fourth decoder/drivers 485 and 487. The reset input to the J-K flip flop 495 is connected in common with the lamp test input to the decoder/drivers 485 and 487 and to the test pin 411. A fourth and fifth, seven-segment displays 499 and 501 are connected to ground and to the third and fourth decoder/drivers in a conventional manner wherein the third driver 485 drives the fourth display 499 and the fourth driver 487 drives the fifth display 501.

The complementary output of the J-K flip flop 495 is connected in parallel to the inputs of a fifth and sixth inverter 503 and 505. The outputs of these inverters 503 and 505 drive the "1's" segments of a sixth seven segment display 507. This sixth display 507 is also connected to the display voltage. The displays 499, 501, and 507 form part of the display 127 of FIG. 1 with the display 499 presenting "units", the display 501 presenting "tens" and the display 507 presenting "hundreds".

By permitting the adjustment of both the oxygen valve 119 and the nitrous oxide valve 219 independently and separately from one another, both as to increasing and decreasing the cross-sectional opening of the valve, minute adjustments may be made in the percentage mix of the gas supplied to the patient. The electronic percent calculation circuitry of FIG. 5 instantly computes this mix. The alphanumeric digital display presented by the display 127 and implemented by the seven segment elements 407, 435, 437, 499, 501, and 507 present a digital presentation of flow rate and percentage gas which can be read in only one way and interpreted in only one manner regardless of the viewpoint of the observer. This provides the advantage not available with analog readouts wherein with digital readout the angle of observation of the observer does not vary the interpretation of the digital reading. Moreover, this digital readout eliminates any interpolation which the observer must make with analog scales.

Figure 6:
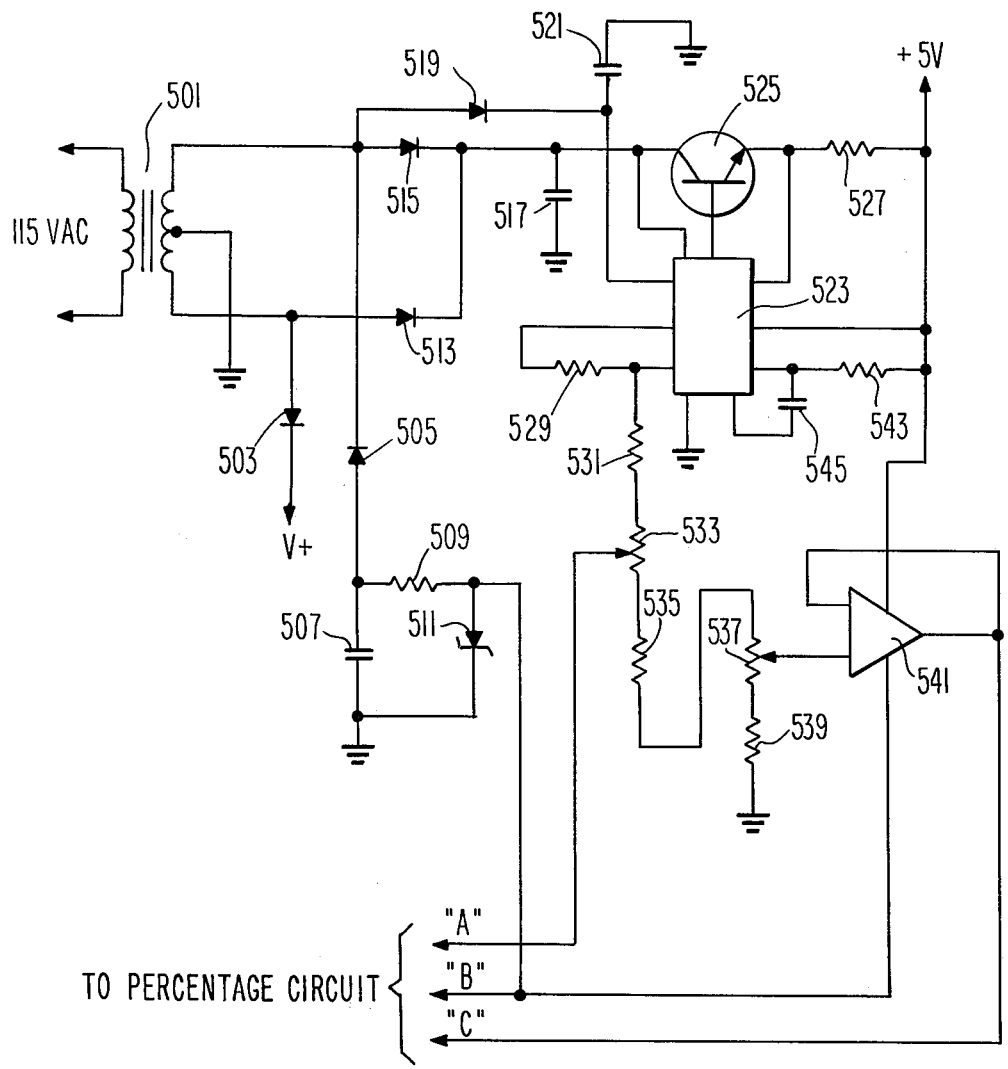
FIG. 6 is a circuit diagram for the power supply of the apparatus.

The detailed circuitry presented in connection with FIGS. 4 and 5 are driven by a regulated power supply, FIG. 6. This power supply includes a transformer 501 with its primary connected to 115 volts AC supply and its secondary having a center tap grounded to develop the maximum 7 ½ volts from the center tap to either output. A fifteenth diode 503 is connected to one end of the secondary of transformer 501 in forward polarity to deliver the supply voltage "V+" for the circuitry of FIGS. 4 and 5. This supply voltage therefore takes the shape of a 60 cycle rectified 7 ½ volt signal. A sixteenth diode 505 is connected to the other end of the secondary winding of transformer 501 in series with a 290 microfarad capacitor 507 to ground. The diode 505 has its anode connected adjacent to the capacitor 507. Connected in parallel across the capacitor 507 to ground is the series connection, a 220 Ohm resistance 509 and a 4.7 volt zener diode 511 with the anode of zener diode 511 adjacent to the resistance 509. Resistor 509 and capacitor 507 act as a filter to shape the negative going half wave rectified signal from the transformer to provide a DC voltage signal. The diode 511 acts to clamp the value of that signal at 4.7 volts. The connection point of the resistance 509 to the zener diode 511 establishes connection voltage "B" to the rest of the circuitry, FIG. 5.

A seventeenth diode 513 is connected with its anode to the anode of diode 503. An eighteenth diode 515 is connected with its anode connected to the cathode of diode 505. The cathodes of diodes 513 and 515 are connected in common, and connected to ground across a 3000 microfarad capacitor 517. A nineteenth diode 519 is connected with its anode to the anode of diode 515. The cathode of diode 519 is connected to ground through a 290 microfarad capacitor 521 and to a first input to a Motorolla-type "MC1723" regulator 523.

The circuit configuration is as recommended by the manufacture to be used with a pass transistor 525 and a 0.33 Ohm current limiting resistor 527.

The necessary voltages required by the analog part of the circuitry are supplied by the resistance network comprising resistors 529, 531, 533, 535, 537, 539; as follows:

| | |
|---|---|
| R529 | 6.2K Ohms |
| R531 | 8.2K Ohms |
| R533 | 500 Ohms |
| R535 | 2.7K Ohms |
| R537 | 200 Ohms |
| R539 | 2.7K Ohms |

An operational amplifier 541 is used as a buffer on the "+1 volt" reference from the resistance network.

While the control apparatus structure described herein is directed to the preferred embodiment and certain alternatives thereto, many changes can be made in the embodiments presented without departing from the intent and scope thereof. It is intended, therefore, that this disclosure be considered in the illustrative sense and not in a limiting sense.

What is Claimed is:

1. Analgesia/anesthesia apparatus comprising in combination the following:
   separate gas flow lines and associated means for connection of said lines to separate supplies of at least two gases;
   means, in each said line, for varying the rate of gas flow through said line;
   encoder means, coupled to said gas flow rate varying means, for encoding the state thereof;
   first means for visual display responsive to the output of said encoder means;
   calculator means, coupled to said gas flow rate varying means, for generating signals representative of the ratio of one of said rates of gas flows to the total gas rate of flow; and
   separate second means for visual display of said ratio responsive to said generated signals.

2. The apparatus of claim 1 wherein said first and second means for visual display each include a digital display.

3. The apparatus of claim 2 wherein said encoder means and said calculator means each include digital circuitry.

4. The apparatus of claim 3 wherein each of said gas flow rate varying means is capable of independent and separate operation.

5. The apparatus of claim 4 also including:
   means, in each said line, for monitoring for a predetermined low gas pressure in said line;
   means, in each said line, for monitoring for a predetermined high gas pressure in said line, and
   means, connected to said low gas pressure monitoring means and connected to said high gas pressure monitoring means, for alarming low and high gas pressures.

6. The apparatus of claim 5 also including:
   means, in each said line, for on-off control of said rate of gas flow, one of said on-off control means being manually operated;
   means for sensing the state of said manually operated on-off control means, said sensing means connected to each of said other on-off control means for directing their state identical to the state of said manually operated on-off control means.

7. The apparatus of claim 6 wherein said digital encoder means includes:
   means, coupled with said gas flow rate varying means, for providing a plurality of electric signals representative of the state thereof; and
   means for encoding a digital signal as a function of said plurality of electric signals received thereby.

8. The apparatus of claim 7 wherein said separate gas flow lines number at least two and wherein said gas flow rate varying means in each said line includes a valve.

9. The apparatus of claim 8 wherein said on-off valve positioned downstream from said low and said high gas pressure monitoring means.

10. The apparatus of claim 9 also including means for regulating the pressure of said gas immediately upstream from each said gas flow rate varying means valve, said regulating means establishing a regulated pressure in each said line independent of the regulated pressure in another said line.

11. The apparatus of claim 10 wherein said plurality of electric signals providing means includes: means, associated with each said valve, for transforming the gate position of each said valve to affect said plurality of electric signals.

12. The apparatus of claim 11 wherein said first digital display includes: a plurality of displays, each display being capable of displaying one digit and being driven by an output from said digital signal encoding means.

13. The apparatus of claim 12 wherein said transforming means includes:
   a control shaft associated with each said valve and being an extension of said valve gate operating shaft;
   a control knob mounted on each said control shaft to rotate said shaft and operate said gate to change said connected valve position, and
   at least one electric wafer switch mounted on each said shaft, said wafer switch having its electric contact points connected to said digital signal encoding means.

14. The apparatus of claim 13 wherein said calculator means includes:
   means for computing percentage flow responsive to the valve position of one of said valves and to the positions of all said valves, said computing means being connected to each said electric wafer switch.

15. The apparatus of claim 14 wherein said second digital display is driven by said computing means output.

16. Control apparatus for administration of anesthetic gas, comprising:
   means for connecting to said anesthetic gas, including a separate gas flow line;
   means, connected to said connecting means, for varying the volume of said anesthetic gas flowing through said gas flow line;
   means for computing the flow rate of said anesthetic gas responsive to the status of said anesthetic gas volume varying means;
   means for digitally displaying said flow rate computed;
   means for connecting to a second gas, including a second separate gas flow line;
   means for varying the volume of said second gas flowing through said second separate gas flow line;
   means for computing the flow rate of said second gas responsive to the status of said second gas volume varying means;
   means for digitally displaying said second gas flow rate computed being driven by said computing means;
   means, responsive to the status of said anesthetic gas varying means and said second gas varying means, for calculating the percentage volume administered of one of said gases with respect to the total volume of both; and
   means, operably associated with said percentage calculating means, for digitally displaying said percentage calculated.

17. Control apparatus for administration of anesthetic gas, comprising:
   means for connecting to said anesthetic gas, including a separate gas flow line;
   means, connected to said connecting means, for varying the volume of said anesthetic gas flowing through said gas flow line;
   means for computing the flow rate of said anesthetic gas responsive to the status of said anesthetic gas volume varying means;
   means for displaying said flow rate computed;
   means for connecting to a second gas, including second separate gas flow line;
   means for varying the volume of said second gas flowing through said second separate gas flow line;
   means for computing the flow rate of said second gas responsive to the status of said second gas volume varying means;
   means for displaying said second gas flow rate computed being driven by said computing means;
   means, responsive to the status of said anesthetic gas varying means and said second gas varying means, for calculating the percentage volume administered of one of said gases with respect to the sum total volume of gas flow; and
   means, operably associated with said percentage calculating means, for digitally displaying said percentage calculated.

18. A flow control system for an analgesic/anesthesia apparatus having gas delivery lines, comprising:
   at least two independent gas flow lines, a separate gas flow rate adjustment component within each said line capable of individually and independently adjusting the flow rate of gas, an alphanumeric display of a percentage of a particular gas flow rate to the total gas flow rate, said alphanumeric display being responsive to each of said individual flow rate adjustments, a separate digital display responsive to each of said flow rate adjustments, wherein each display is individually driven by a separate calculation component responsive to an individual flow rate adjustment, and wherein each separate calculation component responsive to an individual flow rate adjustment includes a digital encoder.

19. The apparatus in claim 18 wherein said alphanumeric display of percentage gas mixture includes a percentage calculation circuit responsive to each of the individual flow rate adjustments.

* * * * *

UNITED STATES PATENT OFFICE
CERTIFICATE OF CORRECTION

Patent No. 4,215,409   Dated  July 29, 1980

Inventor(s)  Robert J. Strowe

It is certified that error appears in the above-identified patent and that said Letters Patent are hereby corrected as shown below:

Column 2, line 32, "with" should be --will--;

Column 2, line 41, "presice" should be --precise--;

Column 7, line 45, after "position" add --from position--,

Column 8, line 34, "diode" should be --anode--,

Column 8, line 45, "HAND" should be --NAND--,

Column 9, line 27, "from" should be --form--,

Column 9, line 59, "utilized" should be --utilizes--,

Column 10, lines 24 and 25, "Motoralla-type "14333B'"" should be --Motorolla-type "14333B"--, Column 10, line 36, after "volt" add --full--, Column 10, line 63, after "the" add --first--, Column 11, line 43, after "cycle" add --half way--, Column 13, line 14, after "on-off" add --control means in each said line includes an on-off--.

Signed and Sealed this

Third Day of March 1981

[SEAL]

Attest:

Attesting Officer

RENE D. TEGTMEYER

Acting Commissioner of Patents and Trademarks